(12) United States Patent
Conlon et al.

(10) Patent No.: US 7,758,598 B2
(45) Date of Patent: Jul. 20, 2010

(54) COMBINATION KNOTTING ELEMENT AND SUTURE ANCHOR APPLICATOR

(75) Inventors: Sean P. Conlon, Loveland, OH (US); Christopher Paul Swain, London (GB)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 406 days.

(21) Appl. No.: 11/437,864

(22) Filed: May 19, 2006

(65) Prior Publication Data

US 2007/0270889 A1   Nov. 22, 2007

(51) Int. Cl.
*A61B 17/04* (2006.01)
(52) U.S. Cl. .............. 606/148; 606/232; 606/300; 606/301; 606/187; 606/104
(58) Field of Classification Search .......... 606/148, 606/232, 300, 301, 187, 104; 604/57, 59, 604/60; 289/17
See application file for complete search history.

(56) References Cited

U.S. PATENT DOCUMENTS

| | | | | |
|---|---|---|---|---|
| 4,235,238 A * | 11/1980 | Ogiu et al. | .................. | 606/145 |
| 4,669,473 A | 6/1987 | Richards et al. | | |
| 4,741,330 A | 5/1988 | Hayhurst | | |
| 4,808,169 A * | 2/1989 | Haber et al. | ................. | 604/195 |
| 5,041,129 A | 8/1991 | Hayhurst et al. | | |
| 5,046,513 A | 9/1991 | Gatturna et al. | | |
| 5,269,809 A | 12/1993 | Hayhurst et al. | | |
| 5,304,184 A * | 4/1994 | Hathaway et al. | ........... | 606/144 |
| 5,307,924 A | 5/1994 | Manosalva et al. | | |
| 5,341,823 A | 8/1994 | Manosalva et al. | | |
| 5,464,425 A | 11/1995 | Skiba | | |
| 5,470,337 A | 11/1995 | Moss | | |
| 5,591,202 A | 1/1997 | Slater et al. | | |
| 5,626,614 A * | 5/1997 | Hart | ........................... | 606/232 |
| 5,630,824 A | 5/1997 | Hart | | |
| 5,755,730 A | 5/1998 | Swain et al. | | |
| 5,800,445 A | 9/1998 | Ratcliff et al. | | |
| 5,899,921 A | 5/1999 | Caspari et al. | | |
| 5,902,321 A | 5/1999 | Caspari et al. | | |
| 5,908,429 A * | 6/1999 | Yoon | ........................... | 606/144 |
| 5,954,747 A | 9/1999 | Clark | | |
| 6,068,648 A | 5/2000 | Cole et al. | | |
| 6,086,608 A * | 7/2000 | Ek et al. | ..................... | 606/232 |
| 6,200,329 B1 | 3/2001 | Fung et al. | | |
| 6,231,592 B1 | 5/2001 | Bonutti et al. | | |

(Continued)

FOREIGN PATENT DOCUMENTS

EP     1447052     8/2004

(Continued)

*Primary Examiner*—(Jackie) Tan-Uyen T Ho
*Assistant Examiner*—Son Dang

(57) ABSTRACT

A medical device that includes a cannulated needle, a first knotting element portion releaseably engaged with the needle, a second knotting element portion also releaseably engaged with the needle, a knotting element deployment actuator that abuts the second knotting element portion, and an anchor deployment actuator in communication with the interior of the needle, wherein the knotting element deployment actuator and anchor actuator are slidably manipulable from a proximal handle of the device, and held in a coaxial relationship with each other. The first knotting element portion may be releaseably engaged by means including shearing posts and adhesives, and the second knotting element portion may be releaseably engaged by means including detents and adhesives.

10 Claims, 8 Drawing Sheets

U.S. PATENT DOCUMENTS

| | | |
|---|---|---|
| 6,368,334 B1 | 4/2002 | Sauer |
| 6,500,184 B1 | 12/2002 | Chan et al. |
| 6,524,328 B2 | 2/2003 | Levinson |
| 6,566,484 B2 | 5/2003 | Gharda et al. |
| 6,663,639 B1 | 12/2003 | Laufer et al. |
| 6,699,263 B2 * | 3/2004 | Cope .......................... 606/232 |
| 6,881,816 B2 | 4/2005 | Gharda et al. |
| 6,909,015 B2 | 6/2005 | Kemmish et al. |
| 7,048,755 B2 | 5/2006 | Bonutti et al. |
| 7,112,207 B2 | 9/2006 | Allen et al. |
| 2003/0158581 A1 | 8/2003 | Levinson |
| 2003/0163160 A1 | 8/2003 | O'Malley et al. |
| 2003/0171760 A1 | 9/2003 | Gambale |
| 2003/0191497 A1 | 10/2003 | Cope |
| 2003/0236535 A1 | 12/2003 | Onuki et al. |
| 2004/0093023 A1 | 5/2004 | Allen et al. |
| 2004/0122473 A1 * | 6/2004 | Ewers et al. ................ 606/222 |
| 2004/0133238 A1 | 7/2004 | Cerier |
| 2004/0153103 A1 | 8/2004 | Schwartz et al. |
| 2004/0186514 A1 | 9/2004 | Swain et al. |
| 2004/0204724 A1 | 10/2004 | Kissel et al. |
| 2004/0260344 A1 | 12/2004 | Lyons et al. |
| 2005/0043746 A1 * | 2/2005 | Pollak et al. ................ 606/144 |
| 2005/0234512 A1 | 10/2005 | Nakao |
| 2005/0251157 A1 * | 11/2005 | Saadat et al. ................ 606/153 |
| 2005/0251202 A1 | 11/2005 | Ewers et al. |
| 2005/0251206 A1 * | 11/2005 | Maahs et al. ................ 606/232 |
| 2005/0251208 A1 | 11/2005 | Elmer et al. |
| 2006/0009789 A1 | 1/2006 | Gambale et al. |
| 2006/0015125 A1 | 1/2006 | Swain |
| 2006/0079914 A1 | 4/2006 | Modesitt et al. |
| 2006/0106405 A1 | 5/2006 | Fann et al. |
| 2007/0112385 A1 | 5/2007 | Conlon |
| 2007/0198021 A1 * | 8/2007 | Wales .......................... 606/86 |

FOREIGN PATENT DOCUMENTS

| | | |
|---|---|---|
| EP | 1447052 A2 | 8/2004 |
| EP | 1484021 A1 | 12/2004 |
| EP | 1598018 A1 | 11/2005 |
| EP | 1632186 | 3/2006 |
| EP | 1632186 A1 | 3/2006 |
| JP | 2004-358045 | 12/2004 |
| WO | 94/22381 | 10/1994 |
| WO | 94022381 A1 | 10/1994 |
| WO | 01/66001 | 9/2001 |
| WO | 01066001 A2 | 9/2001 |
| WO | 01/89393 | 11/2001 |
| WO | 01089393 A1 | 11/2001 |
| WO | 02/094108 | 11/2002 |
| WO | 02094108 A2 | 11/2002 |
| WO | 2006/044837 | 4/2006 |
| WO | 06044837 A2 | 4/2006 |

* cited by examiner

COMBINATION KNOTTING ELEMENT AND SUTURE ANCHOR APPLICATOR

FIELD OF THE INVENTION

The present application relates to surgical fasteners and devices for approximating and fastening tissue and, more particularly, to suture anchors, knotting elements, and associated devices for endoscopically suturing tissue.

BACKGROUND

Endoscopic microsurgery, including procedures performed by way of endoscopic instruments such as gastroscopes, colonoscopes, laparoscopes, and the like, may be preferred as an alternative to open surgery due to the many advantages attributed to such "minimally invasive" techniques, such as shortened hospital stays, reduced recovery time, reduced risk of complications, and diminishment of the amount of and/or visibility of scarring caused by a surgical intervention. In many endoscopic procedures, as in open surgery, there are instances where a surgeon may desire to repair damaged or diseased tissues by apposing the tissues together using a suture. However the suturing devices, stapling devices, and other fastener applicators that have been developed to aid surgeons performing open surgery generally cannot be easily redesigned to be passed through a flexible endoscopic instrument, which may have a working channel having an internal diameter in the range of about 2.5 to about 4.0 millimeters. In addition, surgeons performing endoscopic procedures generally cannot simultaneously manipulate multiple devices fed through such working channels with sufficient ease to permit them to routinely emulate the "pass and catch" suturing techniques that may be employed in open surgery.

To address these problems, various suture anchors and applicator devices have been developed to permit surgeons to endoscopically emplace sutures within tissues. Such suture anchors may be deployed using applicator devices that are inserted within and extended through the working channel of an endoscope, carrying a suture anchor to the site of repair. Such applicators typically include a cannulated needle portion which permits the surgeon to penetrate the tissues adjacent to diseased or damaged tissue and deploy the suture anchor within, or preferably onto a distal surface of, the tissue to be apposed in a repair. The suture anchor is generally attached to a distal end of a suture, with the bulk of the suture extending alongside or within a portion of the applicator device, and with a proximal end of the suture trailing outside the endoscopic instrument. The surgeon may deploy multiple suture anchors around the site of repair by serially passing multiple applicators through a flexible endoscope to the site of repair, or by repeatedly passing and withdrawing a single applicator that may be serially reloaded with additional suture anchors. After deploying the suture anchors, the surgeon may appose the tissue by applying traction to the proximal ends of the sutures, thereby manipulating the suture anchors and the surrounding tissue, and secure the apposed tissue by advancing a series of half hitches towards the site of repair using a knot pusher device. Alternately, the surgeon may thread the trailing ends of the sutures through one of a number of types of knotting elements and associated knotting element applicators, feed the applicator through the flexible endoscope towards the apposed tissue, and "fire" the applicator to fix or "knot" the sutures in place with the knotting element. The reader will appreciate that such procedures may require the repeated insertion, operation, and withdrawal of multiple endoscopic devices, which may increase the complexity of the endoscopic procedure as well as the complexity of equipment inventory and management within the operating environment.

Accordingly, there is a need for an applicator device that provides a means to deploy and implant multiple suture anchors without requiring repeated withdrawal of the device. In addition, there is a need for an applicator device that provides a means to knot the sutures associated with deployed suture anchors without requiring the withdrawal of an anchor applicator device and/or the substitution of a separate knotting element applicator device.

SUMMARY OF THE INVENTION

In one aspect, a combination knotting element and suture anchor applicator is provided and includes a cannulated needle, a first knotting element portion releaseably engaged with the needle, a second knotting element portion also releaseably engaged with the needle, a knotting element deployment actuator that abuts the second knotting element portion, and an anchor deployment actuator in communication with the interior of the needle, wherein the knotting element deployment actuator and anchor deployment actuator are slidably manipulable from a proximal handle of the applicator, and held in a coaxial relationship with each other. The first knotting element portion may be releaseably engaged by a shear post engaged with a shear port on the cannulated needle, and the second knotting element portion may be releaseably engaged by a retaining post engaged with a detent on the cannulated needle.

In another aspect, a combination knotting element and suture anchor applicator is provided and includes a cannulated needle, a first knotting element portion releaseably engaged with the needle, a second knotting element portion also releaseably engaged with the needle, a knotting element deployment actuator that abuts the second knotting element portion, and an anchor deployment actuator in communication with the interior of the needle, wherein the knotting element deployment actuator and anchor deployment actuator are slidably manipulable from a proximal handle of the applicator, and held in a coaxial relationship with each other. The first knotting element portion and second knotting element portion may be releaseably engaged with the cannulated needle by retention posts adhered to the cannulated needle by a frangible adhesive layer.

DETAILED DESCRIPTION OF THE INVENTION

Figure 1:
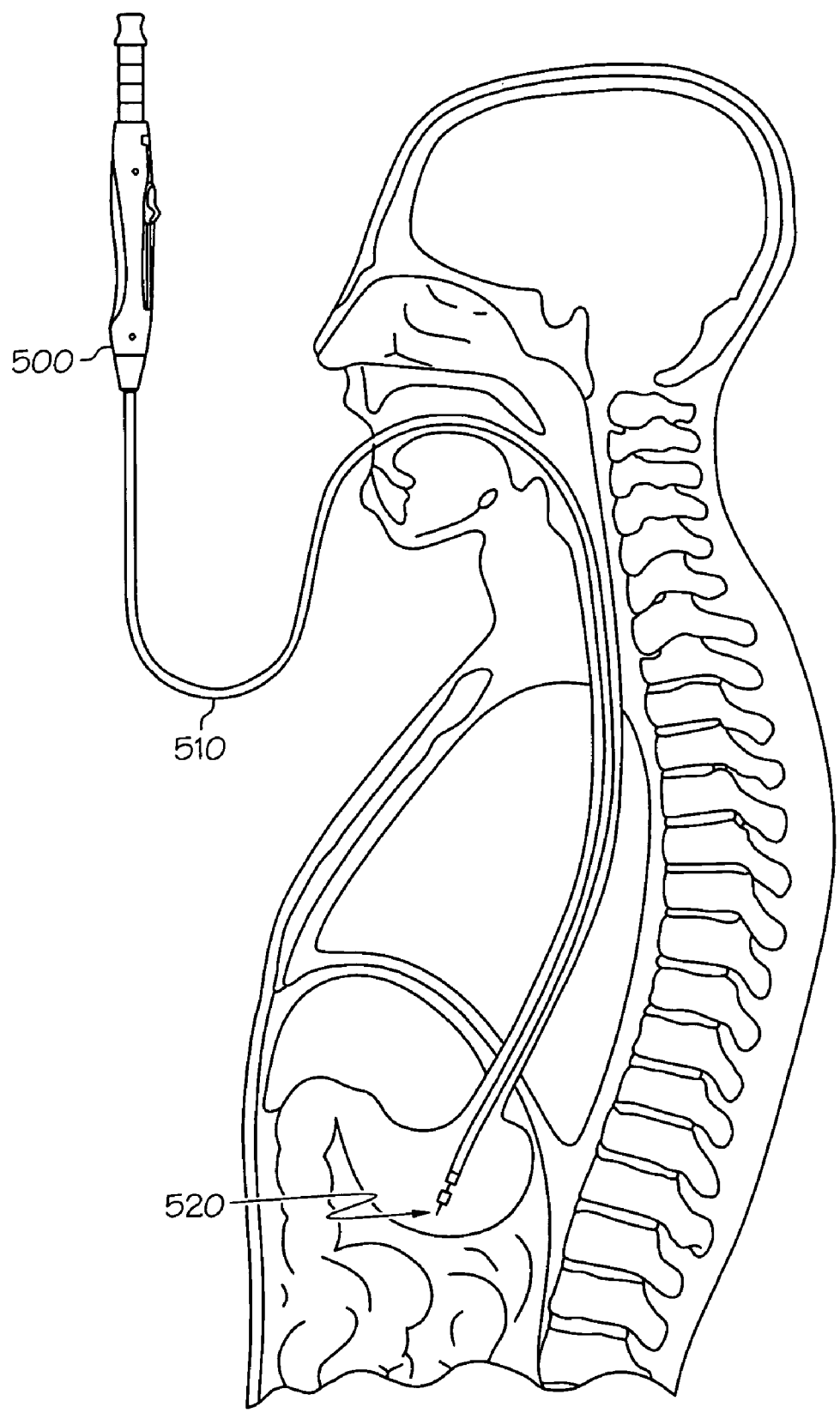
FIG. 1 is a side view of a knotting element and suture anchor applicator device, illustrating a hypothetical use of the device in an endoscopic surgical procedure. The endoscope and endoscopic examination tube are omitted for clarity.

With reference to FIG. 1, the knotting element and suture anchor applicator device disclosed herein generally includes a proximal handle 500 that provides a surgeon with means to manipulate the endoscopic portion of the device at the site of repair; a flexible shaft 510 that includes multiple actuators that provide means for communicating such manipulation to the endoscopic portion of the device; and a distal tip 520 that carries suture anchors, knotting elements, and the like to the site of repair. Flexible shaft 510 may be adapted for insertion into the working channel of a flexible endoscope (not shown) such as a gastroscope or a colonoscope by being flexible, having an outer diameter in a range of about 2.0 to about 3.8 millimeters, and having a length of approximately 1.5 meters. Distal tip 520 may be similarly adapted for insertion into the working channel of a flexible endoscope by having a maximum outer diameter in a range of about 2.0 to about 3.8 millimeters. The reader will appreciate that devices having various diameters and/or lengths may be inserted through other endoscopic instruments, such as laparoscopes, depending on the requirements of the surgical procedure to be performed.

First Aspect of the Device

Figure 2:
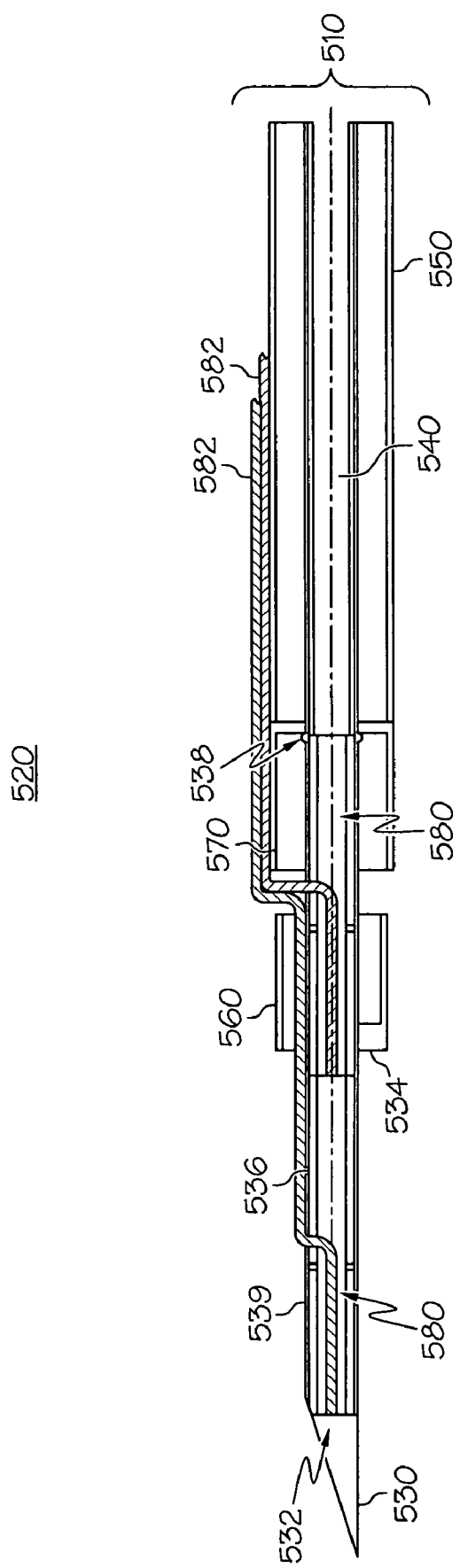
FIG. 2 is a cross sectional side view of the distal tip of a first aspect of the device.
Figure 3:
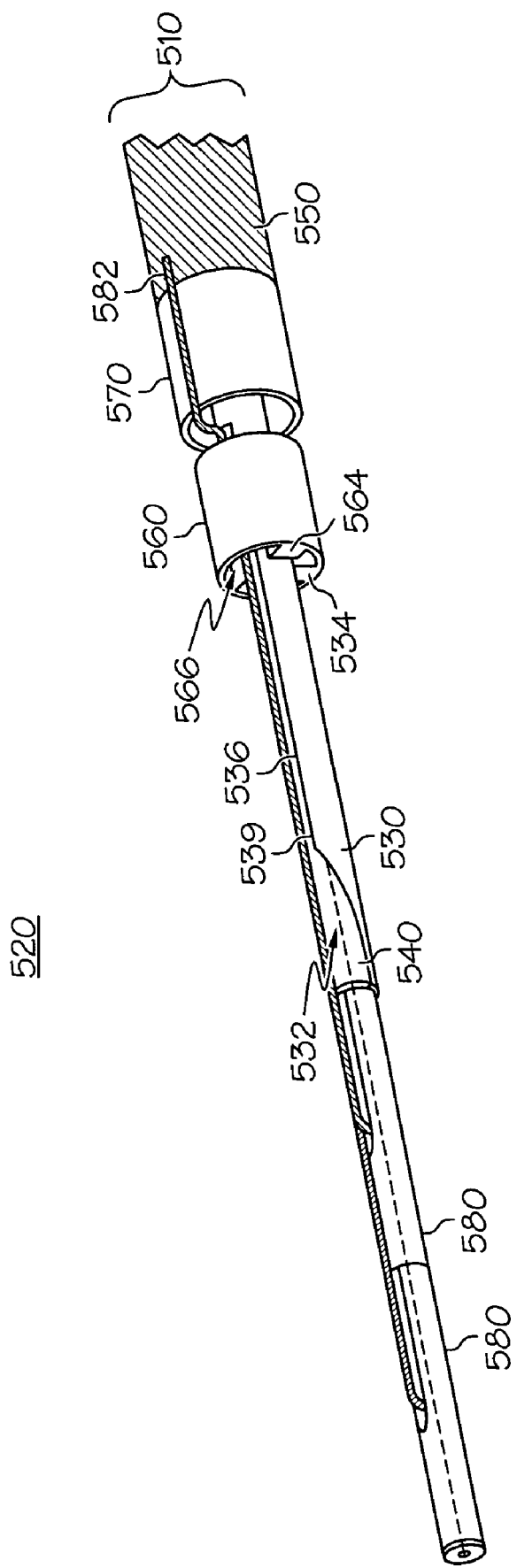
FIG. 3 is a perspective view of the distal tip shown in FIG. 2. The surgical anchors are shown in an expelled state for clarity.

With reference to FIGS. 2 and 3, in one aspect of the device the distal tip 520 of the knotting element and suture anchor applicator device may include a cannulated needle 530, an anchor deployment actuator 540, a knotting element deployment actuator 550, a first knotting element portion 560, and a second knotting element portion 570. Cannulated needle 530 may be manufactured from 19 gage stainless steel hypodermic tubing having an outer diameter of approximately 0.043 inches (1.09 millimeters) and a wall thickness of approximately 0.003 inches (0.076 millimeters). The hypodermic tubing may extend through flexible shaft 510 to proximal handle 500, or alternately may be joined to a second length of metal or extruded plastic polymer tubing extending through flexile shaft 510 to proximal handle 500. Cannulated needle 530 may be joined to such a second length of tubing by welding, gluing, or other methods known in the art. The distal end of cannulated needle 530 may optionally be ground to form a penetrating tip.

Cannulated needle 530 may include a central channel 532, one or more shear ports 534, a suture slot 536 extending proximally from the distal end of the needle, and a detent 538. Central channel 532 is open to the environment at the distal end of cannulated needle 530 and may extend proximally to handle 500. Shear ports 534 in cannulated needle 530 may be disposed around a portion of the needle to provide a means for attaching first knotting element portion 560 to the needle. Suture slot 536 may be provided as a means for routing sutures 582 extending from suture anchors 580 out of central channel 532 and away from the distal tip of cannulated needle 530. Such routing may advantageously reduce interference between cannulated needle 530, suture 582, and suture anchor 580 during the deployment of an anchor, and may advantageously reduce the potential for the distal tip of the needle to sever sutures 582 that would otherwise be routed around that tip. Optionally, the edges of suture slot 536 may be coated with a protective material 539 such as an epoxy resin or a plastic polymer to reduce any potential for the edges of suture slot 536 to sever a suture 582 during operation of the device. Detent 538 may be disposed around a portion of cannulated needle 530 to provide a means for attaching and retaining second knotting element portion 570. Detent 538 may be formed as an integral portion of cannulated needle 530, or alternately may be an annular ring of material affixed to the needle by gluing, welding, or other methods known in the art. Suture anchors 580 may be loaded into central channel 532 and each associated suture 582 may be routed to pass through first knotting element portion 560 and extend outward from second knotting element portion 570 at a location between first knotting element portion 560 and second knotting element portion 570. If cannulated needle 530 includes a suture slot, sutures 582 may additionally be routed to pass through suture slot 536 between first knotting element portion 560 and second knotting element portion 570 and extend outward from second knotting element portion 570. The remainder of each suture 582 may extend alongside knotting element actuator 550 and flexible shaft 510 within the working channel of the endoscope, exiting the instrument adjacent to the proximal handle 500 of the knotting element and suture anchor applicator device.

Anchor deployment actuator 540 may be manufactured from 19 gage stainless steel wire having an outer diameter of approximately 0.036 inches (0.912 millimeters). The actuator 540 may slide within central channel 532, and may extend from approximately the distal end of cannulated needle 530, through central channel 532 and flexible shaft 510, to proximal handle 500. The actuator 540 should have a length sufficient to permit suture anchors 580 to be fully ejected from cannulated needle 530 during a surgical procedure. The actuator 540 may be advanced within central channel 532 in a stepwise manner through the manipulation of a plunger or trigger control on proximal handle 500, or by other control means known in the art. As anchor deployment actuator 540 is advanced, the distal end of the actuator abuts a suture anchor 580, and sufficient advancement will cause the most distally disposed anchor 580 within cannulated needle 530 to be ejected from central channel 532.

Knotting element deployment actuator 550 may be manufactured from a helically wound stainless steel wire or other suitable materials known in the art. The actuator 550 may slide over cannulated needle 530, and may extend from distal tip 520, abutting second knotting element portion 570, to proximal handle 500. The knotting element deployment actuator 550, anchor deployment actuator 540, and cannulated needle 530 may be held in a coaxial relationship along flexible shaft 510 between distal tip 520 and proximal handle 500. The actuator 550 should have a length sufficient to permit first knotting element portion 560 and second knotting element portion 570 to be deployed off the distal end of cannulated needle 530 at the completion of a knotting step in a surgical procedure. The actuator 550 may be advanced over cannulated needle 530 through the manipulation of a control on proximal handle 500 such as a slider or a ratcheting trigger, or by other control means known in the art.

Figure 4:
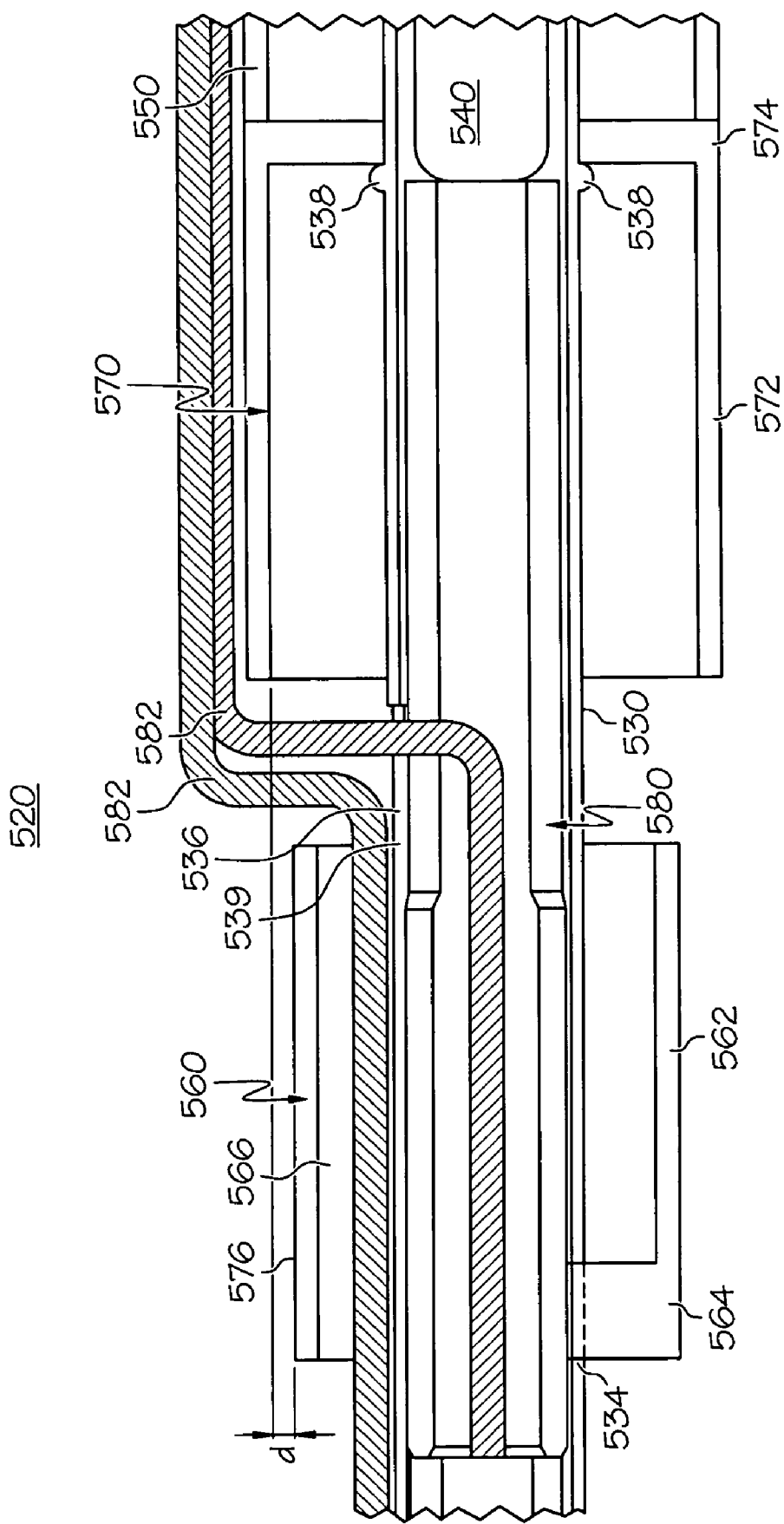
FIG. 4 is a cross sectional side view of the distal tip shown in FIG. 2.

With reference to FIGS. 3 and 4, first knotting element portion 560 may be configured as a partially hollow cylinder having an outer wall 562 and one or more shear posts 564 which may extend inward from outer wall 562 to engage with shear ports 534 of cannulated needle 530. First knotting element portion 560 may provide an interior suture path 566 which contributes to a knotting action described later. First knotting element portion 560 may be constructed from various plastic polymers approved for medical use. The width and number of shear posts 564 may be varied along with other factors, such as the elasticity of the material used to construct the element, to vary the shear force necessary to overcome the engagement of shear posts 564 with shear ports 534. The reader will appreciate that the configuration of this element as a partially hollow cylinder is merely a matter of convenience, and that a variety of shapes may be adapted to define an interior suture path 566 and achieve similar functional results.

Second knotting element portion 570 may also be configured as a generally hollow cylinder having an outer wall 572 and one or more retention posts 574 which may extend inward and engage with detent 538 of cannulated needle 530. Optionally, a single retention post 574 may extend inward from the periphery of outer wall 572 towards cannulated needle 530, forming a retention post similar in structure to a proximal wall. Second knotting element portion 570 may be constructed from various plastic polymers approved for medical use. The width and number of retention posts may be varied along with other factors, such as the degree to which detent 538 projects outward from cannulated needle 530 and the elasticity of the material used to construct the element, to vary the force necessary to overcome the engagement of retention posts 574 with detent 538. The reader will appreciate that the configuration of this element as a generally hollow cylinder is again merely a matter of convenience, and that a variety of shapes may be selected to complement the shape of first knotting element portion 560 and achieve similar functional results.

Typically, outer wall 572 of second knotting element portion 570 has an inner diameter approximately equal to the outer diameter of outer wall 562 of first knotting element portion 560 with the addition of a gap, d. Preferably, outer wall 572 has an inner diameter in the range of about the outer diameter of outer wall 562 to about the sum of the outer diameter of outer wall 562 and the diameter of a suture line. The knotting element may be engaged by slidingly joining first knotting element portion 560 and second knotting element portion 570, such that first knotting element portion 560 nests within second knotting element portion 570, leaving a suture gap 576 having a width approximately equal to gap d defined between the outer surface of outer wall 562 of first knotting element portion 560 and the inner surface of outer wall 572 of second knotting element portion 570. Sutures 582 extending through interior suture path 566 of first knotting element portion 560 are bent by the joining of the knotting element portions to conform to an "S"-shaped path that runs through interior suture path 566, around the proximal end of first knotting element portion 560, through suture gap 576, around the distal end of second knotting element portion 570, and along flexible shaft 510 towards proximal handle 500. Sutures 582 are retained or "knotted" within the joined knotting element portions by frictional engagement with the outer surface of outer wall 562 of first knotting element portion 560 and the inner surface of outer wall 572 of second knotting element portion 570, and optionally by engagement between the proximal end of first knotting element portion 560 and the distal surface of retention posts 574. Similarly, first knotting element portion 560 and second knotting element portion 570 are retained in a joined relation by frictional engagement with each other and sutures 582. Optionally, the outer surface of outer wall 562 of first knotting element portion 560 and the inner surface of outer wall 572 of second knotting element portion 570 may be textured, coated, or otherwise modified to increase the apparent coefficient of friction between the two surfaces, and between the surfaces and sutures 582.

Figure 5:
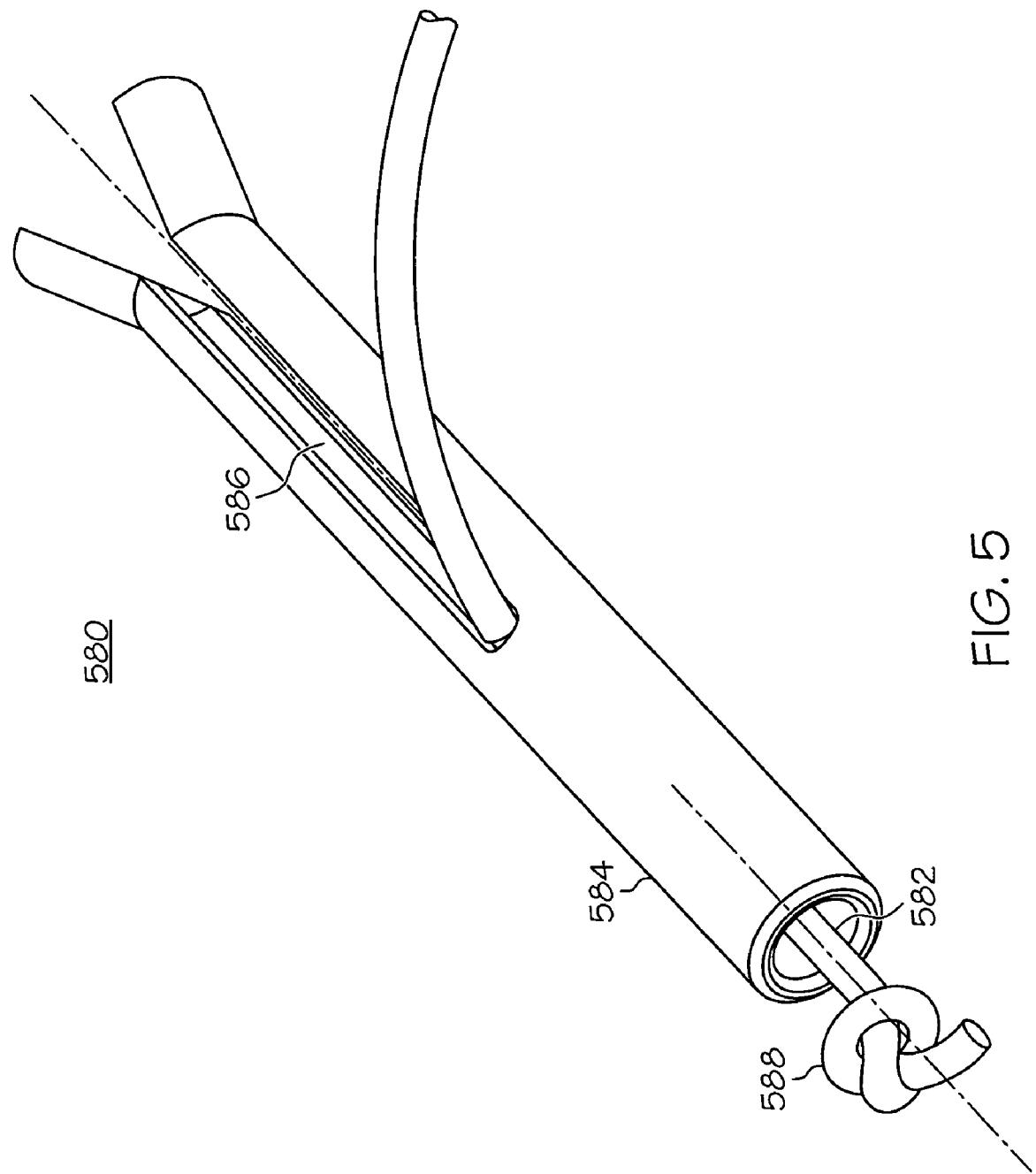
FIG. 5 is a perspective view of a suture anchor.

A plurality of suture anchors 580 may be loaded into central channel 532 of cannulated needle 530. With reference to FIG. 5, such suture anchors may include conventional T-tags having a hollow cylindrical body 584 including a longitudinal slot 586 extending along approximately one half of the length of the body. Suture 582 may be attached to suture anchor 580 by passing the suture through body 584 and forming a knot 588 in suture 582 larger than the diameter of body 584, or alternately by crimping, gluing, or otherwise affixing suture 582 within body 584 adjacent to slot 586. The reader will appreciate that a variety of different suture anchors may be deployed from the knotting element and suture anchor applicator device disclosed herein, including but not limited to the expandable suture anchors disclosed in my copending application, U.S. patent application Ser. No. 11/274,358, entitled "Expandable Suture Anchor" and filed on Nov. 15, 2005, the entire contents of which are incorporated herein by reference.

Second Aspect of the Device

Figure 6:
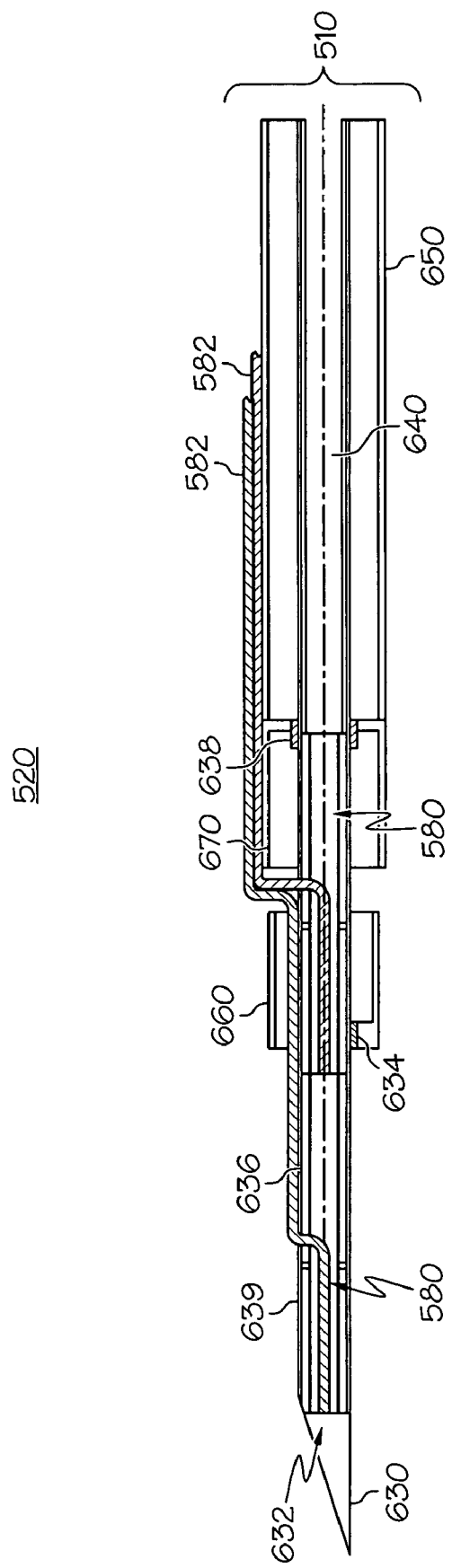
FIG. 6 is cross sectional side view of the distal tip of a second aspect of the device.
Figure 7:
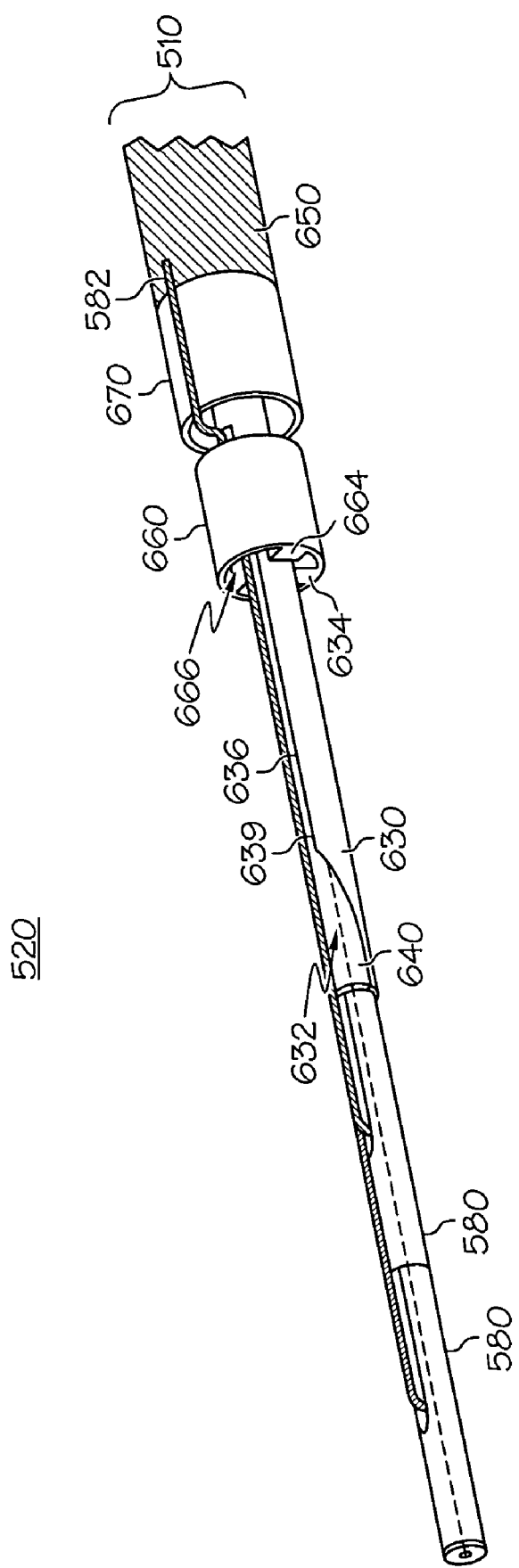
FIG. 7 is a perspective view of the distal tip shown in FIG. 6. The surgical anchors are shown in an expelled state for clarity.
Figure 8:
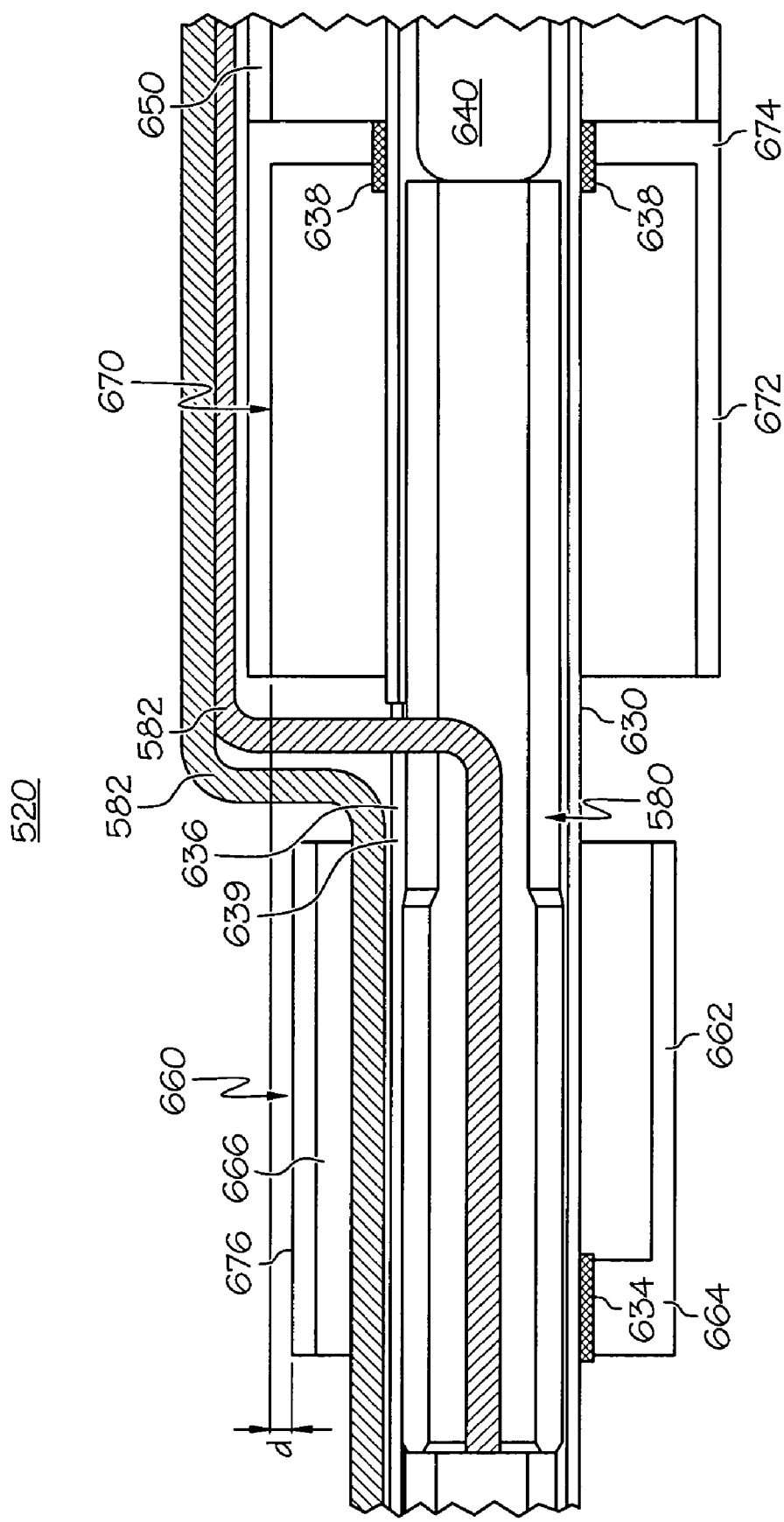
FIG. 8 is a cross sectional side view of the distal tip shown in FIG. 6.

With reference to FIGS. 6 and 7, in an additional aspect of the device the distal tip 520 of the knotting element and suture anchor applicator device may include a cannulated needle 630, an anchor deployment actuator 640, a knotting element deployment actuator 650, a first knotting element portion 660, and a second knotting element portion 670. Cannulated needle 630 may be manufactured from 19 gage stainless steel hypodermic tubing having an outer diameter of approximately 0.043 inches (1.09 millimeters) and a wall thickness of approximately 0.003 inches (0.076 millimeters). The hypodermic tubing may extend through flexible shaft 510 to proximal handle 500, or alternately may be joined to a second length of metal or extruded plastic polymer tubing extending through flexile shaft 510 to proximal handle 500. Cannulated needle 630 may be joined to such a second length of tubing by welding, gluing, or other methods known in the art. The distal end of cannulated needle 630 may optionally be ground to form a penetrating tip.

Cannulated needle 630 may include a central channel 632 and a suture slot 636 extending proximally from the distal end of the needle. Central channel 632 is open to the environment at the distal end of cannulated needle 630 and may extend proximally to handle 500. Suture slot 636 may be provided as a means for routing sutures 582 extending from suture anchors 580 out of central channel 632 and away from the distal tip of cannulated needle 630. Such routing may advantageously reduce interference between cannulated needle 630, suture 582, and suture anchor 580 during the deployment of an anchor, and may advantageously reduce the potential for the distal tip of the needle to sever sutures 582 that would otherwise be routed around that tip. Optionally, the edges of suture slot 636 may be coated with a protective material 639 such as an epoxy resin or a plastic polymer to reduce any potential for the edges of suture slot 536 to sever a suture 582 during operation of the device. Suture anchors 580 may be loaded into central channel 632 and each associated suture 582 may be routed to pass through first knotting element portion 660 and extend outward from second knotting element portion 670 at a location between first knotting element portion 660 and second knotting element portion 670. If cannulated needle 630 includes a suture slot, sutures 582 may additionally be routed to pass through suture slot 636 between first knotting element portion 660 and second knotting element portion 670 and extend outward from second knotting element portion 670. The remainder of each suture 582 may extend alongside knotting element actuator 650 and flexible shaft 510 within the working channel of the endoscope, exiting the instrument adjacent to the proximal handle 500 of the knotting element and suture anchor applicator device.

Anchor deployment actuator 640 may be manufactured from 19 gage stainless steel wire having an outer diameter of approximately 0.036 inches (0.912 millimeters). The actuator 640 may slide within central channel 632, and may extend from approximately the distal end of cannulated needle 630, through central channel 632 and flexible shaft 510, to proximal handle 500. The actuator 640 should have a length sufficient to permit suture anchors 580 to be fully ejected from cannulated needle 630 during a surgical procedure. The actuator 640 may be advanced within central channel 632 in a stepwise manner through the manipulation of a plunger or trigger control on proximal handle 500, or by other control means known in the art. As anchor deployment actuator 640 is advanced, the distal end of the actuator abuts a suture anchor 580, and sufficient advancement will cause the most distally disposed anchor 580 within cannulated needle 630 to be ejected from central channel 632.

Knotting element deployment actuator 650 may be manufactured from a helically wound stainless steel wire or other suitable materials known in the art. The actuator 650 may slide over cannulated needle 630, and may extend from distal tip 520, abutting second knotting element portion 670, to proximal handle 500. The knotting element deployment actuator 650, anchor deployment actuator 640, and cannulated needle 630 may be held in a coaxial relationship along flexible shaft 510 between distal tip 520 and proximal handle 500. The actuator 650 should have a length sufficient to permit first knotting element portion 660 and second knotting element portion 670 to be deployed off the distal end of cannulated needle 630 at the completion of a knotting step in a surgical procedure. The actuator 650 may be advanced over cannulated needle 630 through the manipulation of a control on proximal handle 500 such as a slider or a ratcheting trigger, or by other control means known in the art.

With reference to FIGS. 3 and 4, first knotting element portion 660 may be configured as a partially hollow cylinder having an outer wall 662 and one or more retention posts 664 which may extend inward from outer wall 662 to abut cannulated needle 630. First knotting element portion 660 may be engaged with cannulated needle 630 by affixing one or more retention posts 664 to cannulated needle 630 at the point where the posts abut the needle with a frangible layer of adhesive 634. First knotting element portion 660 may provide an interior suture path 666 which contributes to a knotting action described later. First knotting element portion 660 may be constructed from various plastic polymers approved for medical use. The width and number of retention posts 664 may be varied along with other factors, such as the strength of the frangible adhesive 634 binding the posts to cannulated needle 630, to vary the shear force necessary to overcome the engagement of retention posts 664 and cannulated needle 630. The reader will appreciate that the configuration of this element as a partially hollow cylinder is merely a matter of convenience, and that a variety of shapes may be adapted to define an interior suture path 666 and achieve similar functional results.

Second knotting element portion 670 may also be configured as a generally hollow cylinder having an outer wall 672 and one or more retention posts 674 which may extend inward and abut cannulated needle 630. Optionally, a single retention post 674 may extend inward from the periphery of outer wall 672 towards cannulated needle 630, forming a retention post similar in structure to a proximal wall. Second knotting element portion 670 may be engaged with cannulated needle 630 by affixing one or more retention posts 674 to cannulated needle 630 at the point where the posts abut the needle with a frangible layer of adhesive 638. Second knotting element portion 670 may be constructed from various plastic polymers approved for medical use. The width and number of retention posts 674 may be varied along with other factors, such as the strength of the frangible adhesive 638 binding the posts to cannulated needle 630, to vary the force necessary to overcome the engagement of the retention posts 674 with cannulated needle 630. The reader will appreciate that the configuration of this element as a generally hollow cylinder is again merely a matter of convenience, and that a variety of shapes may be selected to complement the shape of first knotting element portion 660 and achieve similar functional results.

Typically, outer wall 672 of second knotting element portion 670 has an inner diameter approximately equal to the outer diameter of outer wall 662 of first knotting element portion 660 with the addition of a gap, d. Preferably, outer wall 672 has an inner diameter in the range of about the outer diameter of outer wall 662 to about the sum of the outer diameter of outer wall 662 and the diameter of a suture line. The knotting element may be engaged by slidingly joining first knotting element portion 660 and second knotting element portion 670, such that first knotting element portion 660 nests within second knotting element portion 670, leaving a suture gap 676 having a width approximately equal to gap d defined between the outer surface of outer wall 662 of first knotting element portion 660 and the inner surface of outer wall 672 of second knotting element portion 670. Sutures 582 extending through interior suture path 666 of first knotting element portion 660 are bent by the joining of the knotting element portions to conform to an "S"-shaped path that runs through interior suture path 666, around the proximal end of first knotting element portion 660, through suture gap 676, around the distal end of second knotting element portion 670, and along flexible shaft 510 towards proximal handle 500. Sutures 582 are retained or "knotted" within the joined knotting element portions by frictional engagement with the outer surface of outer wall 662 of first knotting element portion 660 and the inner surface of outer wall 672 of second knotting element portion 670, and optionally by engagement between the proximal end of first knotting element portion 660 and the distal surface of retention posts 674. Similarly, first knotting element portion 660 and second knotting element portion 670 are retained in a joined relation by frictional engagement with each other and sutures 582. Optionally, the outer surface of outer wall 662 of first knotting element portion 660 and the inner surface of outer wall 672 of second knotting element portion 670 may be textured, coated, or otherwise modified to increase the apparent coefficient of friction between the two surfaces, and between the surfaces and sutures 582.

Illustrative Use of an Aspect of the Device

The knotting element and suture anchor applicator device disclosed herein may be used to endoscopically appose tissues in the following illustrative, but not limiting manner. A surgeon may guide an endoscopic instrument, such as a gastroscope and examination tube, through the gastrointestinal tract of a patient. The surgeon may then use the endoscopic instrument to survey the patent's internal tissues, such as a stomach, and to visualize damaged tissue, such as an ulcerated region. To effect a repair, the surgeon may obtain a knotting element and suture anchor applicator loaded with a plurality of suture anchors 580 and associated sutures 582, such as the T-tags described previously, and insert distal tip 520 and flexible shaft 510 of the device into the working channel of the instrument, guiding distal tip 520 to the site of repair. The surgeon may then manipulate distal tip 520 to cause cannulated needle 530 to penetrate the tissues adjacent to the damaged tissue, and manipulate suture anchor actuator 540 to deploy a first suture anchor 580 onto a distal surface of, or optionally within, a first portion of the tissue to be apposed. The surgeon may then manipulate distal tip 520 to cause cannulated needle 530 to penetrate other tissues adjacent to the damaged tissue, and manipulate suture anchor actuator 540 to deploy a second suture anchor 580 onto a distal surface of, or optionally within, a second portion of the tissue to be apposed without withdrawing distal tip 520 from the endoscopic instrument to swap in a second device or to reload a suture anchor 580 into cannulated needle 530. Thus, the surgeon may emplace a plurality of suture anchors 580 without withdrawing the device. Preferably, the knotting element and suture anchor applicator is loaded with 2, 3, or 4 suture anchors 580 and associated sutures 582. After deploying the last suture anchor 580, the surgeon may manipulate the proximal ends of the sutures 582 to appose the tissues at the site of repair. When the tissues have been properly apposed, the surgeon may "fire" the knotting element by manipulating knotting element actuator 550 and applying force to second knotting element portion 570, which is in engagement with cannulated needle 530 as described previously. If sufficient force is applied, retention posts 574 of second knotting element portion 570 may distort and become released from engagement with detent 538 of cannulated needle 530, permitting second knotting element portion 570 to slide towards the distal end of the needle until it abuts first knotting element portion 560, which is in engagement with cannulated needle 530 as described previously. The joining of first knotting element portion 560 and second knotting element portion 570 will "knot" sutures 582 as described previously. Continued manipulation of knotting element actuator 550 will transmit force through second knotting element portion 570 to first knotting element portion 560, transforming the applied force into a shear force acting across shear posts 564. If sufficient force is transmitted, shear posts 564 may shear and become released from engagement with shear ports 534 of cannulated needle 530, permitting first knotting element portion 560 and joined second knotting element portion 570 to slide towards the distal end of the needle until the joined knotting element portions are deployed off the distal end of cannulated needle 530. The surgeon may withdraw distal tip 520 and flexible shaft 510 from the endoscopic instrument to clear the working channel of the instrument in preparation for additional procedures or in preparation for the withdrawal of the instrument.

Although various aspects of the disclosed device have been shown and described herein, modifications may occur to those skilled in the art upon reading this specification. The present application includes such modifications as are within the spirit of the invention, and is to be limited only by the scope of the appended claims.

What is claimed is:

1. A combination knotting element and suture anchor applicator, the applicator comprising:
   a cannulated needle;
   a first knotting element portion releaseably engaged with said needle;
   a second knotting element portion releaseably engaged with said needle;
   a knotting element deployment actuator abutting said second knotting element portion; and
   an anchor deployment actuator in communication with the interior of said needle;
   wherein said knotting element deployment actuator and said anchor deployment actuator are slidably manipulable from a proximal handle of said applicator, and said knotting element deployment actuator and said anchor deployment actuator are held in a coaxial relationship with each other;
   wherein said knotting element deployment actuator and said anchor deployment actuator are independently manipulable from the proximal handle of said applicator.

2. The combination knotting element and suture anchor applicator of claim 1, further comprising a plurality of suture anchors carried within a distal end of said cannulated needle.

3. The combination knotting element and suture anchor applicator of claim 1, wherein said cannulated needle includes a shear port and said first knotting element includes a shear post engaged with said shear port, whereby an applied force may be used to release said first knotting element portion from engagement with said cannulated needle.

4. The combination knotting element and suture anchor applicator of claim 3, wherein said first knotting element is released by an applied force transmitted through said second knotting element.

5. The combination knotting element and suture anchor applicator of claim 1, wherein said first knotting element includes a shear post engaged with said cannulated needle by a frangible adhesive layer, whereby an applied force may be used to release said first knotting element portion from engagement with said cannulated needle.

6. The combination knotting element and suture anchor applicator of claim 5, wherein said first knotting element is released by an applied force transmitted through said second knotting element.

7. The combination knotting element and suture anchor applicator of claim 1, wherein said cannulated needle includes a detent and said second knotting element includes a retaining post engaged with said detent, whereby an applied force may be used to release said second knotting element portion from engagement with said cannulated needle.

8. The combination knotting element and suture anchor applicator of claim 7, wherein said second knotting element is released by an applied force transmitted through said knotting element deployment actuator.

9. The combination knotting element and suture anchor applicator of claim 1, wherein said second knotting element includes a retaining post engaged with said cannulated needle by a frangible adhesive layer, whereby an applied force may be used to release said second knotting element portion from engagement with said cannulated needle.

10. The combination knotting element and suture anchor applicator of claim 9, wherein said second knotting element is released by an applied force transmitted through said knotting element deployment actuator.

* * * * *